United States Patent

Loccufier et al.

Patent Number: 5,558,974
Date of Patent: Sep. 24, 1996

[54] PHOTOGRAPHIC MATERIAL CONTAINING A NEW TYPE OF HYDRAZIDE

[75] Inventors: Johan Loccufier, Zwijnaarde; Hieronymus Andriessen, Beerse, both of Belgium

[73] Assignee: Agfa-Gevaert, N.V., Mortsel, Belgium

[21] Appl. No.: 399,594

[22] Filed: Mar. 7, 1995

[30] Foreign Application Priority Data

Mar. 11, 1994 [EP] European Pat. Off. ............ 94200632

[51] Int. Cl.$^6$ ........................................... G03C 1/06
[52] U.S. Cl. ........................ 430/264; 430/598; 430/607
[58] Field of Search ............................. 430/264, 598, 430/607; 548/309.7

[56] References Cited

U.S. PATENT DOCUMENTS 3,655,391  4/1972  Merli et al. .................. 430/607
5,204,214  4/1993  Okamura et al. .................. 430/264
5,270,334  12/1993  O'Sullivan et al. .................. 514/459

FOREIGN PATENT DOCUMENTS 0436027  10/1991  European Pat. Off. .

*Primary Examiner*—Geraldine Letscher
*Attorney, Agent, or Firm*—Breiner & Breiner

[57] ABSTRACT

A new type of hydrazide compounds is disclosed corresponding to general formula (A):

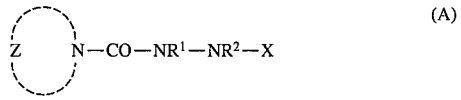

the symbols of which are explained in the description. Examples of synthesis are given. Incorporation of these diacyl hydrazides into the silver halide emulsion layer(s) of a photographic material causes a significant increase in sensitivity.

6 Claims, No Drawings

PHOTOGRAPHIC MATERIAL CONTAINING A NEW TYPE OF HYDRAZIDE

DESCRIPTION

1. Field of the Invention

The present invention relates to a new class of hydrazide compounds and to photographic materials containing these compounds.

2. Background of the Invention

One of the most evident and permanent goals of photographic silver halide emulsion technology consists in ever further improving sensitivity without rising fog and without being obliged to increase the average emulsion grain size which would result in increased granularity. This permanent goal is known by photographic scientists as optimization of the grain-fog-sensitivity relationship.

The term sensitivity can apply to the intrinsic blue or near-ultraviolet sensitivity or to the sensitivity in a defined spectral region. The spectral sensitivity depends on the intrinsic sensitivity and the efficiency of the spectral sensitizer used. The intrinsic sensitivity can be influenced by emulsion parameters, by coating parameters, by external factors, by developer parameters, and by the presence or absence of particular ingredients in the coated layer or in the developer. As already indicated the best known emulsion parameter influencing sensitivity is the average grain size. To a certain limit increasing the average grain size enhances sensitivity simply by increasing the probability of photon absorption. A further important emulsion factor is the optimization of chemical ripening which should create sensitivity specks on the grain surface acting as efficient traps for photoelectrons generated during exposure and thus giving rise to a concentrated developable latent image. As external factors the pH and the pAg at which the coating is performed, the humidity of the environment, the presence of a halogen acceptor and mechanical pressure should be mentioned. Further on, the obtained sensitivity can be influenced by the presence in the developer of so-called development accelerators, e.g. polyalkylene oxides. Finally the sensitivity can be enhanced by the presence in the photographic material or in the developer of particular compounds acting as sensitivity boosters. An especially useful class of the latter compounds is formed by hydrazine and hydrazide derivatives. These compounds are mostly described for incorporation into graphic arts pre-press materials by which dot and line originals should be sharply and faithfully reproduced with so-called lith quality. These compounds are mostly used in connection with so-called "hard dot Rapid Access" processing systems. Such systems provide alternatives for classical lith development which suffers from complicated replenishment problems. Patent literature of recent years is replete with disclosures of new hydrazide classes and applications thereof. Specific new hydrazide derivatives are described, e.g. in JP-A 57-99635, EP 0 217 310, JP-A 61-270744, JP-A 62-89958, EP 0 283 040, EP 0 301 799, U.S. Pat. Nos. 4,816,373, 4,847,180, JP-A 63-294552, JP-A 63-44649, JP-A 63-8715, EP 0 283 040, JP-A 01-100530, EP 0 345 025, JP-A 01-201650, EP 0 356 898, DE 38 29 078, U.S. Pat. Nos. 4,950,578, 5,028,510, EP 0 399 460, U.S. Pat. No. 5,006,445, JP-A 01-285940, U.S. Pat. Nos. 4,988,604, 4,994,365, JP-A 02-300474, JP-A 02-302750, JP-A 02-841, JP-A 02-947, EP 0 444 506, EP 0 479 156, JP-A 04-283743, EP 0 539 925 and U.S. Pat. No. 5,212,045.

The present invention extends the teachings on hydrazide compounds in photographic silver halide materials.

It is an object of the present invention to provide a new class of hydrazide derivatives capable of acting as sensitivity boosters.

It is a further object of the present invention to provide photographic materials with improved sensitivity.

SUMMARY OF THE INVENTION

The objects of the present invention are realized by providing a photographic material comprising a support and at least one silver halide emulsion layer, characterized in that said emulsion layer contains a compound according to general formula (A):

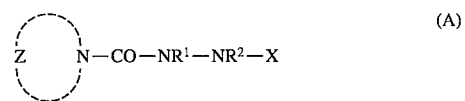

wherein

Z represents the necessary atoms to close a substituted or unsubstituted heterocyclic ring which is either a five-membered ring containing at least two heteroatoms or a six-membered ring, which ring may carry one or more fused-on rings, and which ring must contain a C—H bond permitting oxidative aromatisation to an acyl-onium group by means of a hydride shift or a consecutive 2-electron-proton transfer:

each of $R^1$ and $R^2$ independently represents a hydrogen atom or an alkali-labile group giving rise to a hydrogen atom on hydrolysis:

X is an acyl group selected from the group consisting of CO—$R^3$, CS—$R^4$, $SO_2$—$R^5$, PO—$R^6R^7$ and (CN—$R^8$)—$R^9$, wherein each of $R^3$ to $R^9$ independently represents alkyl, aryl, cycloalkyl, heterocycloalkyl, heteroaryl, O-alkyl, O-aryl, O-heteroaryl, O-heterocycloalkyl, S-alkyl, S-aryl, S-heterocycloalkyl, S-heteroaryl, N—$R^{10}R^{11}$ wherein each of $R^{10}$ and $R^{11}$ independently represents hydrogen, aryl, alkyl, heteroaryl, heterocycloalkyl or acyl as defined for X, and wherein all the defined R-groups may carry substituents, and wherein $R^6$ together with $R^7$, and $R^{10}$ together with $R^{11}$ may represent the necessary atoms to close a ring.

DETAILED DESCRIPTION OF THE INVENTION

Examples of particularly interesting subclasses of general formula (A) are listed below (wherein R represents H or any substituent in the heterocyclic rings):

structures derived from pyridine, optionally with fused-on rings; examples:

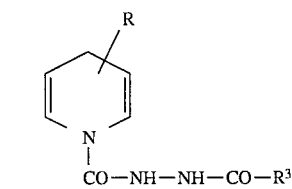

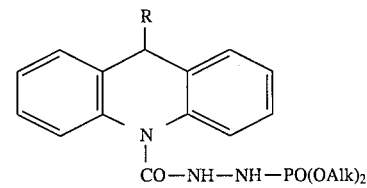

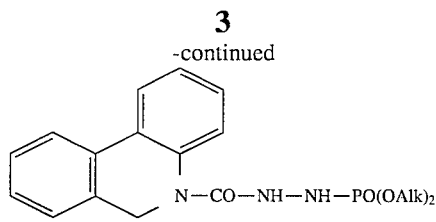

derivatives of imidazoles, optionally with fused-on rings; examples:

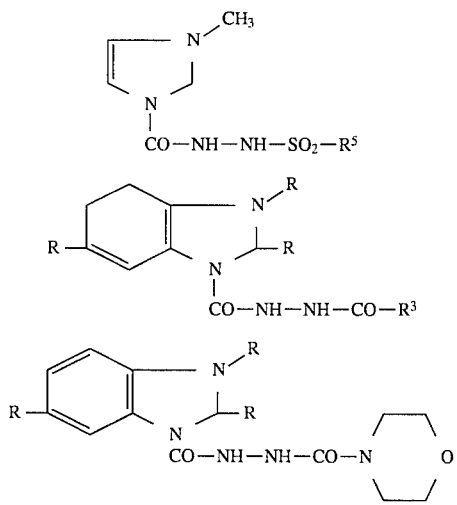

derivatives of thiazoles, optionally with fused-on rings: examples:

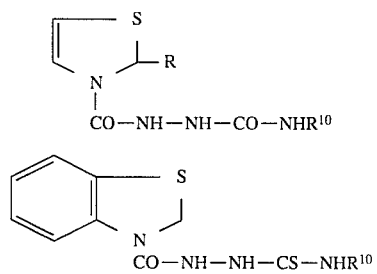

derivatives of pyrazines, optionally with fused-on rings: examples:

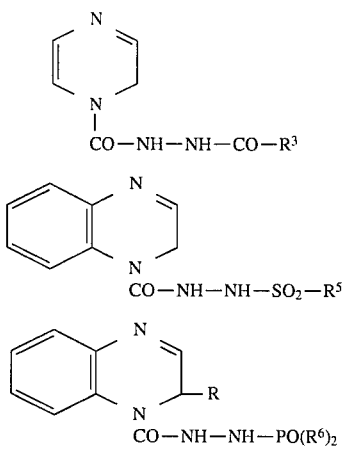

N-alkylpyrrole derivatives, optionally with fused-on rings: examples:

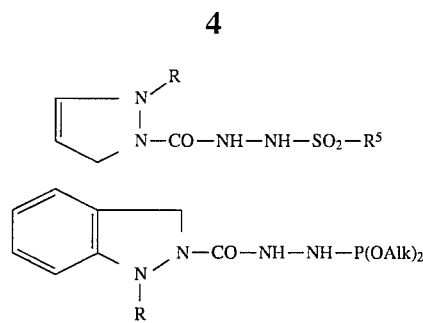

derivatives of oxazoles, optionally with fused-on rings; examples:

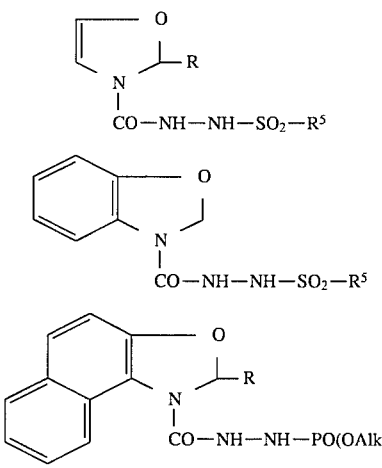

pyrimidine derivatives, optionally with fused-on rings: examples:

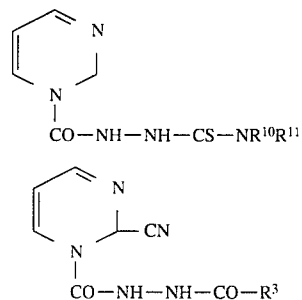

derivatives of N-alkyltriazoles: example:

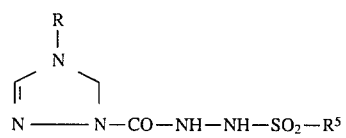

derivatives of oxadiazoles: example:

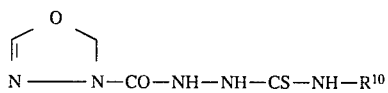

derivatives of thiadiazoles: example:

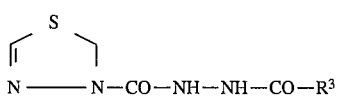

derivatives of pyridiazines, optionally with fused-on rings; examples:

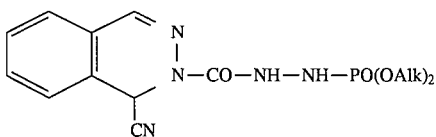

derivatives of isoxazoles and isothiazoles and analogous compounds: examples:

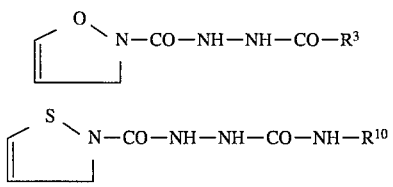

derivatives of selenazoles, optionally with fused-on rings; examples:

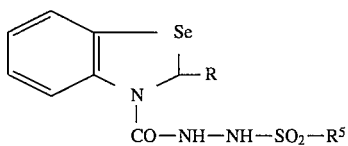

As will be explained in detail further on in the section of synthesis examples the diacyl hydrazides of the present invention can be prepared involving three steps:

step I: reductive acylation of an N-heterocycle by means of a chloroformate;

step II: hydrazinolysis of the carbamates obtained by step I;

step III: condensation reaction of the hydrazides obtained by step II with an appropriate reagent gives the diacyl hydrazide end products.

All claimed heterocycles can be oxidized to an acylonium intermediate. A typical example of such an oxidation has been published by Akiba et al. for N-acyl-dihydropyridine systems (Tetrahedron Letters 24 (47), 5269–5272 (1983), Tetrahedron Letters 26 (27), 3267–3270 (1985)).

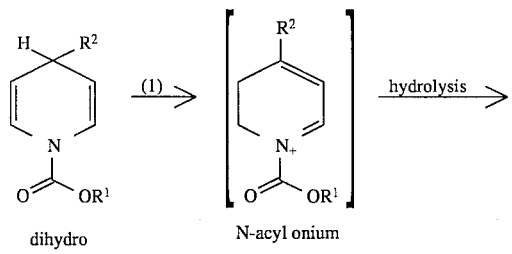

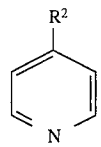

Typical oxidants are $O_2$, $AgNO_3$ and 2,3-dichloro-5,6-dicyano-1,4-benzoquinone. It is obvious that this type of oxidation is not limited to N-acyl-dihydropyridines but can be applied to all claimed heterocycles, as illustrated by N-acyl-benzimidazolines.

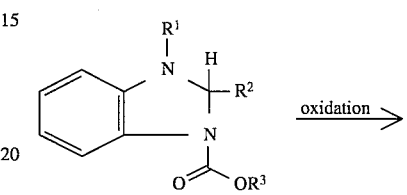

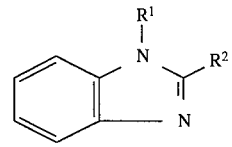

The mechanism of this type of oxidation still is a point of discussion and can be considered either as a hydride shift or as a consecutive 2-electron proton shift as illustated below, depending on the heterocycle and the type of oxidant.

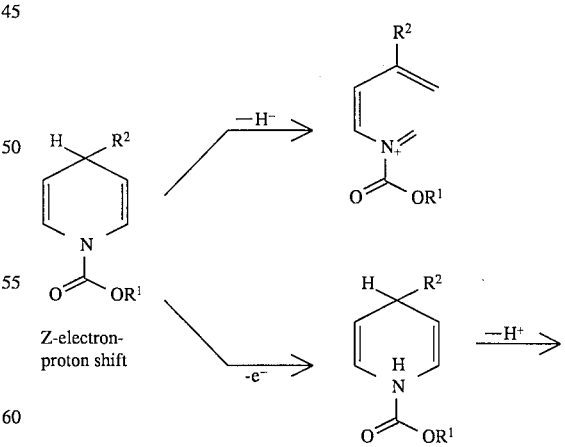

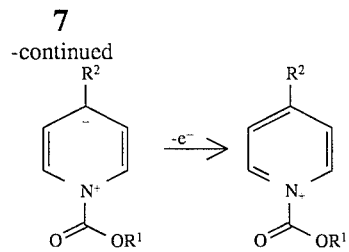

The mechanism of analogous oxidations has been extensively studied for the redox-coenzyme NADH. For benzimidazolines, some mechanistic aspects have been published by Wuest et al. (J. Org. Chem. 52, 5437–5442 (1987), J. Org. Chem. 52, 5443–5446 (1987)).

In a particular preferred embodiment a substituent corresponding to one of $R^3$ to $R^{11}$ or a substituent carried by $R^3$ to $R^{11}$ is a moiety capable of forming a poorly soluble salt or complex with silver ions. In a most preferred embodiment said moiety is a tetrazaindene moiety (see e.g. compound III-1 in the synthesis section of the examples). Such moieties form a so-called "silver anchor" with silver halide and it was experimentally established that these compounds require the incorporation of a smaller amount to be effective than representatives of the other hydrazide subclasses.

The hydrazide compounds of the present invention are incorporated into the emulsion layer(s) of the photographic material in the form of a dispersion or in the form of an aqueous solution depending on their water-solubility.

In principle a mixture of two or more hydrazide compounds can be used but usually just one compound will be sufficient. The hydrazide compound is preferably present in the emulsion layer(s) in a concentration between $10^{-6}$ and $2.10^{-1}$ mol per mol of silver halide.

The formation of the silver halide grains incorporated into the photosensitive emulsion layer occurs according to well-known conventional techniques. They can be prepared by mixing the halide and silver solutions in partially or fully controlled conditions of temperature, concentrations, sequence of addition, and rates of addition. The silver halide can be precipitated according to the single-jet method, the double-jet method, or the conversion method. The resulting silver halide particles may have a regular crystalline form such as a cubic or octahedral form or they may have a transition form. They may also have an irregular crystalline form such as a spherical form or a tabular form, or may otherwise have a composite crystal form comprising a mixture of said regular and irregular crystalline forms. The silver halide grains may have a multilayered grain structure. According to a simple embodiment the grains may comprise a core and a shell which may have different halide compositions and/or may have undergone different modifications such as the addition of dopes. Besides having a differently composed core and shell the silver halide grains may also comprise different phases in between.

The average size of the silver halide grains may range from 0.05 to 1.0 µm, preferably from 0.2 to 0.5 µm. The size distribution of the silver halide particles of the photographic emulsion can be homodisperse or heterodisperse. A homodisperse size distribution is obtained when 95% of the grains have a size that does not deviate more than 30% from the average grain size.

The silver halide emulsion can be chemically ripened as described i.a. in "Chimie et Physique Photographique" by P. Glafkidès, in "Photographic Emulsion Chemistry" by G. F. Duffin, in "Making and Coating Photographic Emulsion" by V. L. Zelikman et al, and in "Die Grundlagen der Photographischen Prozesse mir Silberhalogeniden" edited by H. Frieser and published by Akademische Verlagsgesellschaft (1968). As described in said literature chemical sensitization can be carried out by effecting the ripening in the presence of small amounts of compounds containing sulphur, e.g., thiosulphate, thiocyanate, thioureas, sulphites, mercapto compounds, and rhodamines. The emulsions can be sensitized also by means of gold-sulphur ripeners or by means of reductors, e.g., tin compounds as described in GB 789,823, amines, hydrazine derivatives, formamidine-sulphinic acids, and silane compounds. In a preferred embodiment conventional gold-sulphur ripening agents are used.

The silver halide emulsion(s) can be appropriately spectrally sensitized with methine dyes such as those described by F. M. Hamer in "The Cyanine Dyes and Related Compounds", 1964, John Wiley & Sons. Dyes that can be used for the purpose of spectral sensitization include cyanine dyes, merocyanine dyes, complex cyanine dyes, complex merocyanine dyes, hemicyanine dyes, styryl dyes and hemioxonol dyes. Particularly valuable dyes are those belonging to the cyanine dyes, merocyanine dyes and complex merocyanine dyes.

The halide composition of the silver halide emulsions is not specifically limited and may be any composition selected from silver chloride, silver bromide, silver iodide, silver chlorobromide, silver bromoiodide, and silver chlorobromoiodide.

The silver halide emulsion may comprise compounds preventing the formation of fog or stabilizing the photographic characteristics during the production or storage of photographic elements or during the photographic treatment thereof. Many known compounds can be added as fog-inhibiting agent or stabilizer to the silver halide emulsion. Suitable examples are i.a. the heterocyclic nitrogen-containing compounds such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles (preferably 5-methyl benzotriazole), nitrobenzotriazoles, mercaptotetrazoles, in particular 1-phenyl-5-mercapto tetrazole, mercaptopyrimidines, mercaptotriazines, benzothiazoline-2-thione, oxazoline thione, triazaindenes, tetrazaindenes and pentazaindenes, especially those described by Birr in Z. Wiss. Phot. 47 (1952), pages 2–58, triazolopyrimidines such as those described in GB 1,203,757, GB 1,209,146, JA-Appl. 75-39537, and GB 1,500,278, and 7-hydroxy-s-triazolo[1,5-a]pyrimidines as described in U.S. Pat. No. 4,727,017, and other compounds such as benzenethiosulphonic acid, benzenethiosulphinic acid and benzenethiosulphonic acid amide. Other compounds that can be used as fog-inhibiting compounds are metal salts such as, e.g., mercury or cadmium salts and the compounds described in Research Disclosure N° 17643 (1978), Chapter VI.

The fog-inhibiting agents or stabilizers can be added to the silver halide emulsion prior to, during, or after the ripening thereof and mixtures of two or more of these compounds can be used.

Besides the silver halide another essential component of a light-sensitive emulsion layer is the binder. The binder is a hydrophilic colloid, preferably gelatin. This gelatin can be lime-treated or acid-treated gelatin. The preparation of such gelatin types has been described in e.g. "The Science and Technology of Gelatin", edited by A. G. Ward and A. Courts, Academic Press 1977, page 295 and next pages. The gelatin can also be an enzyme-treated gelatin as described in Bull. Soc. Sci. Phot. Japan, N° 16, page 30 (1966). The gelatin can contain calcium or can be substantially free of calcium.

Gelatin can, however, be replaced in part or integrallly by synthetic, semi-synthetic, or natural polymers. Synthetic substitutes for gelatin are e.g. polyvinyl alcohol, poly-N-vinylpyrrolidone, polyvinylimidazole, polyvinylpyrazole, polyacrylamide, polyacrylic acid, and derivatives thereof, in particular copolymers thereof. Natural substitutes for gelatin are e.g., other proteins such as zein, albumin and casein, cellulose, saccharides, starch, and alginates. In general, the semi-synthetic substitutes for gelatin are modified natural products e.g. gelatin derivatives obtained by conversion of gelatin with alkylating or acylating agents or by grafting polymerizable monomers on gelatin, and cellulose derivatives such as hydroxyalkylcellulose, carboxymethylcellulose, phtaloylcellulose, and cellulosesulphates.

The binders of the photographic element, especially when the binder is gelatin, can be hardened with appropriate hardening agents such as those of the epoxide type, those of the ethylenimine type, those of the vinylsulphone type, e.g., 1,3-vinylsulphonyl-2-propanol, chromium salts e.g. chromium acetate and chromium alum, aldehydes, e.g., formaldehyde, glyoxal, and glutaraldehyde, N-methylol compounds, e.g., dimethylolurea and methyloldimethylhydantoin, dioxan derivatives, e.g., 2,3-dihydroxy-dioxan, active vinyl compounds, e.g., 1,3,5-triacryloyl-hexahydro-s-triazine, active halogen compounds e.g. 2,4-dichloro-6-hydroxy-s-triazine, and mucohalogenic acids e.g. mucochloric acid and mucophenoxychloric acid. These hardeners can be used alone or in combination. The binders can also be hardened with fast-reacting hardeners such as carbamoylpyridinium salts as disclosed in U.S. Pat. No. 4,063,952.

When the silver halide emulsions are used in colour photographic material the typical ingredients for this type of material are present, e.g. colour formerd, masking compounds, development inhibitor releasing (DIR) compounds, etc. These ingredients are usually added in the form of a dispersion containing so-called oilformers if necessary.

The photographic emulsion can be coated on a support by means of any of the conventional coating techniques, e.g. dip coating, air-knife coating, extrusion coating, slide-hopper coating and curtain coating.

Beside the light sensitive emulsion layer(s) the photographic material can contain several non light sensitive layers, e.g. an anti-stress top layer, one or more backing layers, and one or more intermediate layers that may containing filter dyes or antihalation dyes that absorb scattering light and thus promote the image sharpness. Suitable light-absorbing dyes are described in i.a. U.S. Pat. Nos. 4,092, 168, 4,311,787, DE 2,453,217, and GB 7,907,440. One or more backing layers can be provided at the non-light-sensitive side of the support. This layers which can serve as anti-curl layer can contain i.a. matting agents e.g. silica particles, lubricants, antistatic agents, light-absorbing dyes, opacifying agents, e.g. titanium oxide and the usual ingredients like hardeners and wetting agents.

The photographic material may further comprise various kinds of surface-active agents in the photographic emulsion layer or in at least one other hydrophilic colloid layer. Suitable surface-active agents include non-ionic agents such as saponins, alkylene oxides, e.g., polyethylene glycol, polyethylene glycol/polypropylene glycol condensation products, polyethylene glycol alkyl ethers or polyethylene glycol alkyl aryl ethers, polyethylene glycol esters, polyethylene glycol sorbitan esters, polyalkylene glycol alkylamines or alkylamides, silicone-polyethylene oxide adducts, glycidol derivatives, fatty acid esters of polyhydric alcohols and alkyl esters of saccharides; anionic agents comprising an acid group such as a carboxy, sulpho, phospho, sulphuric or phosphoric ester group; ampholytic agents such as aminoacids, aminoalkylsulphonic acids, aminoalkyl sulphates or phosphates, alkylbetaines, and amine-N-oxides; and cationic agents such as alkylamine salts, aliphatic, aromatic, or heterocyclic quaternary ammonium salts, aliphatic or heterocyclic ring-containing phosphonium or sulphonium salts. Such surface-active agents can be used for various purposes, e.g., as coating aids, as compounds preventing electric charges, as compounds improving slidability, as compounds facilitating dispersive emulsification, as compounds preventing or reducing adhesion, and as compounds improving the photographic characteristics, e.g., higher contrast, sensitization, and development acceleration.

The photographic element of the present invention may further comprise various other additives such as, e.g., compounds improving the dimensional stability of the photographic element, UV-absorbers, spacing agents and plasticizers.

Suitable additives for improving the dimensional stability of the photographic element are i.a. dispersions of a water-soluble or hardly soluble synthetic polymer, e.g., polymers of alkyl (meth)acrylates, alkoxy (meth)acrylates, glycidyl (meth)acrylates, (meth)acrylamides, vinyl esters, acrylonitriles, olefins, and styrenes, or copolymers of the above with acrylic acids, methacrylic acids, $\alpha,\beta$-unsaturated dicarboxylic acids, hydroxyalkyl (meth)acrylates, sulphoalkyl (meth)acrylates, and styrenesulphonic acids.

The support of the photographic material may be opaque or transparent, e.g., a paper support or resin support. When a paper support is used preference is given to one coated at one or both sides with an $\alpha$-olefin polymer, e.g., a polyethylene layer which optionally contains an anti-halation dye or pigment. It is also possible to use an organic resin support, e.g., cellulose nitrate film, cellulose acetate film, polyvinylacetal film, polystyrene film, polyethylene terephthalate film, polycarbonate film, polyvinyl chloride film or poly-$\alpha$-olefin films such as polyethylene or polypropylene film. The thickness of such organic resin film is preferably comprised between 0.07 and 0.35 mm. These organic resin supports are preferably coated with a subbing layer which can contain water-insoluble particles such as silica or titanium dioxide.

The new hydrazide compounds of the present invention can be used in various types of black-and-white or colour photographic elements such as in photographic elements for graphic arts, e.g., camera materials, scan materials, image-setting materials and contact materials, and for so-called general amateur and professional photography, diffusion transfer reversal photographic elements, cinematographic recording and duplicating films, and radiographic recording and duplicating films. So it is clear that unlike most other hydrazide derivatives their use is not limited to graphic arts materials for "hard dot Rapid Access" development systems.

The photographic materials are to be exposed according to their particular composition and application. Possible exposure sources include tungsten light, xenon light, halogen bulbs, metal-halogen lamps, CRT devices, X-ray sources and laser devices.

The processing cycle of the exposed photographic materials conventionally includes a development step, a fixing step, a washing step and a drying step. In case of colour materials a bleaching or bleach-fixing step is required. In case of black-and-white development the developing solution, or the material itself in case of so-called "activation development", contains a developing agent, e.g., such well-known substances like 1,4-dihydroxybenzene compounds such as hydroquinone, chlorohydroquinone, bromohydroquinone, toluhydroquinone, morpholinemethylhydroquinone and sulphohydroquinone. Apart from the main developing agent an auxiliary developing agent can be used. Typical auxiliary developing agents include 3-pyrazolidone developing agents, e.g. 1-phenyl-3-pyrazolidone, 1-phenyl-4,4-dimethyl-3-pyrazolidone, 1-phenyl-4-methyl-4'-hydroxymethyl-3-pyrazolidone, and N-methyl-p-aminophenol sulphate. In case of colour development p-phenylenediamine derivatives are employed as developing agents. In the fixing or bleach-fixing solution usually ammonium or sodium thiosulphate is employed as fixing agent. Useful bleaching agents for bleach or bleach-fixing baths are ferricyanide ions, persulphate ions and complexes of iron(III) and polyaminocarboxylic acids, e.g. ethylenediamine-tetraacetic acid iron(III)-monosodium salt.

The following examples illustrate the present invention without however limiting it thereto.

EXAMPLES

A. Examples of Synthesis of Diacyl Hydrazides
Step I: Reductive Acylations

Examples of the reaction of an N-heterocycle and a chloroformate giving rise to a carbamate are given in Scheme I (see further on). Depending on the chemical nature of the reagents preparation procedure A or B, explained below, was used.

Preparation Procedure A 0.1 mol of the appropriate N-heterocycle (cf. Scheme I) and 0.2 mol of sodium borohydride were dissolved in 100 ml of tetrahydrofuran (THF). The solution was cooled to −5° C. A solution of 0.15 mol of the appropriate chloroformate (cfr. Scheme I) in 50 ml of THF was added while the temperature was kept below 0° C. The reaction was allowed to continue for 1 h at 0° C. 200 ml of water was carefully added. The reaction mixture was pourred into 500 ml of water and the product was isolated by the appropriate work-up. Actual examples:

Compound I.1: The aqueous layer was extracted twice with 300 ml of methylene chloride. The pooled organic fractions were dried over $MgSO_4$. The $MgSO_4$ was removed by filtration and the solvent was evaporated under reduced pressure. The residue was recrystallized from ethanol.

Compound I.3: The precipitated product was isolated by filtration, recrystallized from 1-methoxy-2-propanol, washed with ethanol and dried under reduced pressure.

Compound I.4: The precipitated product was isolated by filtration, recrystallized from 1-methoxy-2-propanol, washed with methanol and dried under reduced pressure.

Compound I.5: The precipitated product was isolated by filtration and dried under reduced pressure. The product was used without further purification.

Compound I.7: The oily residue was crystallized upon treatment with 40 g of ice and 200 ml of ethanol. The product was recrystallized from ethanol and dried under reduced pressure.

Compound I.8/I.9: The aqueous layer was extracted twice with 300 ml of methylene chloride. The pooled organic fractions were dried over $MgSO_4$. The $MgSO_4$ was removed by filtration and the solvent was evaporated under reduced pressure. The mixture of isomers was further converted without purification.

Preparation Procedure B:

0.1 mol of the appropriate phosphite and 0.25 mol of the appropriate pyridine derivative (cf. Scheme I) were dissolved in 100 ml of toluene. A solution of 0.1 mol of the appropriate chloroformate in 50 ml of toluene was added while the temperature was kept between 10° and 15° C. The chloroformate was added over a period of 20 min. The reaction mixture was stirred for 1 h at room temperature. The product was isolated by the appropriate work-up. Examples:

Compound I.2: The precipitated salts were removed by filtration and washed with a small amount of toluene. The pooled fractions were extracted twice with 100 ml of 1N HCl, once with 100 ml of water and dried over $MgSO_4$. The $MgSO_4$ was removed by filtration and the product was isolated by preparative column chromatography (eluent:methylene chloride/ethyl acetate; $R_f$=0.38).

Compound I.6: The precipitated product was isolated by filtration. The crude product was treated with 50 ml of ethanol and the precipitated slightly yellow product was isolated again by filtration. The product was dried under reduced pressure.

Compound I.10/I.11: Pyridinium chloride was removed by filtration. The filtrate was extracted with 200 ml of water and with 100 ml of 0.1N HCl, dried over $MgSO_4$ and evaporated under reduced pressure. The two isomers were isolated by preparative column chromatography (eluent:ethyl acetate/hexane 90/10).

Step II: Hydrazinolysis of the Carbamates

The different carbamates obtained according to step I were subjected to hydrazinolysis (see Scheme II). Examples:

Compound II.1: 125.5 g of compound 1.1 (0.5 mol) was suspended in 300 ml of ethanol. 50 ml (1 mol) of hydrazine hydrate was added and the reaction mixture was gently refluxed for 4 h. Compound I.1 gradually dissolved. The product was allowed to crystallize over night, isolated by filtration, and dried under reduced pressure.

Compound II.2: 20.6 g of compound 1.6 (0.051 mol) was suspended in 25 ml of methanol. 7.67 ml of hydrazine hydrate (0.153 mol) was added. After 3 min compound 1.6 dissolved, while a yellow product precipitated from the medium. 75 ml of ethyl acetate was added to dissolve the precipitated product. Compound II.2 crystallized from the medium, was isolated by filtration and washed 3 times with 25 ml of ethyl acetate and 3 times with water. The crude product was suspended in 50 ml of 10 % $K_2CO_3$ to remove residual 4-nitrophenol, again isolated by filtration, washed several times with water, and dried under reduced pressure.

Compound II.3: 22.25 g of compound 1.2 (0.05 mol) was dissolved in 25 ml of ethanol. 3.76 ml of hydrazine hydrate (0.075 mol) was added and the reaction was allowed to continue for 1 h at room temperature. The precipitated products were removed by filtration. The filtrate was poured into a solution of 3 g of $K_2CO_3$ in 750 ml of water and extracted twice with 150 ml of methylene chloride. The pooled organic fractions were extracted 4 times with a 1% $K_2CO_3$ solution, dried over $MgSO_4$ and evaporated under reduced pressure. The oily residue was used further on without additional purification.

Compound II.4: 29.9 g of compound 1.3 (0.1 mol) was suspended in 200 ml of ethanol. 7.5 ml (0.15 mol) of hydrazine hydrate was added and the reaction mixture was refluxed for 30 minutes. Compound I.3 gradually dissolved. On cooling down to room temperature, compound II.4 crystallized from the medium, was isolated by filtration, washed with ethanol until the filtrate was colourless and dried under reduced pressure.

Compound II.5: 15.4 g of compound 1.4 (0.05 mol) was suspended in 25 ml of 1-methoxy-2-propanol. 5 ml (0.1 mol) of hydrazine hydrate was added and the reaction mixture was refluxed for 90 minutes. After cooling down, the solvent was removed under reduced pressure and the oily residue was crystallized from methanol.

Compound II.6: 18 g of compound 1.5 (0.05 mol) was suspended in 50 ml of 1-methoxy-2-propanol. 5 ml (0.1 mol) of hydrazine hydrate was added and the reaction mixture was refluxed for 3 hours. After cooling down, the solvent was removed under reduced pressure and the residue was crystallized from methanol.

Compound II.7: 12.5 g of compound 1.7 (0.05 mol) was suspended in 50 ml of ethanol. 3.76 ml hydrazine hydrate was (0.075 mol) added and the reaction mixture was refluxed for two and a half hours. On cooling down, compound II.7 crystallizes from the medium, is isolated by filtration and dried under reduced pressure.

Compound II.8/II.9: 48 g of the isomers I.8/I.9 (0.2 mol) in 100 ml of ethanol was treated with 15 ml of hydrazine hydrate (0.3 mol). The reaction mixture was refluxed for 3 h, poured into 400 ml of water and extracted twice with 100 ml of t.butyl methyl ether. The pooled organic fractions were dried over $MgSO_4$. The $MgSO_4$ was removed by filtration and the solvent was evaporated under reduced pressure. The crude mixture of isomers was used without further purification.

Compound II.10: 10.65 g of compound I.10 (0.029 mol) in 30 ml ethanol is treated with 2.92 ml of hydrazine hydrate (0.058 mol). The reaction mixture was refluxed for 1 h, concentrated to one third of its volume and poured into 100 ml of water. The aqueous layer was extracted twice with 50 ml of t.butyl methyl ether and once with 50 ml of methylene chloride. The pooled organic fractions were dried over $MgSO_4$. The $MgSO_4$ is removed by filtration and the solvent is evaporated under reduced pressure. Compound II.10 was used without further purification.

Compound II.11: 18 g of compound 1.11 (0.06 mol) in 30 ml of ethanol was treated with 6 ml (0.12 mol) of hydrazine hydrate. The reaction mixture was refluxed for 1 hour, concentrated to one third of its volume and poured into 200 ml of water. The mixture was extracted twice with 100 ml of t.butyl-methyl-ether and once with 100 ml methylene chloride. The pooled organic fractions were dried over $MgSO_4$. The $MgSO_4$ was removed by filtration and the solvent was evaporated under reduced pressure. Compound II.11 was used without further purification.

Step III: Diacyl Hydrazides

The chemical reactions involved in the final step in the synthesis of the diacyl hydrazides of the present invention are illustrated in Schemes III and IV (see further on). Depending on the reagents involved preparation procedure A', B', C', D' or E' was used. Examples:

Preparation Procedure A'

0.05 mol of the appropriate hydrazide was suspended in 50 ml of acetonitrile. 0.055 mol of the appropriate acyl halide was added. 0.06 mol of pyridine was added while the temperature was kept below 30 C. The reaction was allowed to continue for 45 min. The product was isolated by the appropriate work-up:

Compound III.3: The reaction mixture was treated with 60 ml of water. The product was isolated by filtration, washed with acetonitrile and methanol, and dried under reduced pressure.

Compound III.4: The product crystallized from the medium on standing overnight at room temperature. The product was isolated by filtration and recrystallized from ethanol.

Compound III.5: The reaction mixture was treated with 200 ml of water. The product was isolated by filtration, washed with water, and ethanol and dried under reduced pressure.

Compound III.9: The reaction mixture was poured into 250 ml of water and extracted twice with 100 ml of ethyl acetate. The pooled ethyl acetate fractions were dried over $MgSO_4$ and the solvent was evaporated under reduced pressure. The oily residue was treated with 15 ml of ethanol and 75 ml of water. The product crystallized from the medium with some difficulty, was isolated by filtration, washed with ethanol/water (1:1), and dried under reduced pressure.

Compound III.10: The reaction mixture was treated with 50 ml of water. The product was isolated by filtration, washed with acetonitrile/water (1:4) and methanol, and dried under reduced pressure.

Compound III.11: 200 ml of water was added and the product crystallized from the medium. The product was isolated by filtration, washed with water, and dried under reduced pressure.

Compound III.14: The reaction mixture was treated with 100 ml of water. The product was isolated by filtration, washed with acetonitrile/water (1:4), water and methanol, and dried under reduced pressure.

Compound III.15: The precipitated product was isolated by filtration and recrystallized from ethanol.

Compound III.16/III.17: The precipitated product was isolated by filtration and the isomers were separated by preparative column chromatography (eluent:methylene chloride/THF 95/5).

Compound III.18: 70 ml of water was added to the reaction mixture. The precipitated product was isolated by filtration and recrystallized from ethyl acetate.

Compound III.19: 150 ml of water was added. Compound III.19 precipitated as a viscous oil. The oily residue was redissolved in 50 ml of methylene chloride. The solution was dried over $MgSO_4$. After removal of the $MgSO_4$, the solvent was evaporated under reduced pressure and the product was isolated by preparative column chromatography (eluent methylene chloride/ethyl acetate 1/1).

Preparation Procedure B'

0.05 mol of the appropriate hydrazide was suspended in 50 ml of acetonitrile. First 0.05 mol of the appropriate acyl halide was added, then of 0.05 mol of pyridine. The reaction mixture was refluxed for 1 h. while all products dissolved. The reaction mixture was allowed to cool and the product was isolated by the appropriate work-up. Examples:

Compound III.6: The product crystallized from the medium, was isolated by filtration, intensively washed with water and methanol, and dried under reduced pressure.

Compound III.12: The reaction mixture was diluted with 50 ml of methanol. The precipitated product was isolated by filtration, washed with acetonitrile/water (1:2) and purified by preparative column chromatography (eluent: methylene chloride/ethyl acetate 90/10; $R_f$=0.52).

Preparation Procedure C'

0.05 mol of the appropriate hydrazide was suspended in 100 ml of acetonitrile. 0.05 mol of the appropriate acyl halide and 0.12 mol of pyridine were added. The reaction was allowed to continue for 4 h at room temperature and the product was isolated by the appropriate work-up.

Compound III.7: The precipitated product was isolated by filtration, treated in refluxing methanol, isolated again by filtration, washed with ethanol, and dried under reduced pressure. Compound III.13: The product was isolated by filtration, washed with acetonitrile and water, and dried under reduced pressure.

Preparation Procedure D'

0.05 mol of the appropriate carboxylic acid was dissolved in 50 ml of dimethylacetamide. 0.06 mol of 1,1'-carbonyldiimidazole (CDI) was added and the reaction mixture was stirred for 1 h at room temperature. 0.05 mol of the appropriate hydrazide was added and the reaction was allowed to continue for 1 h at room temperature. The product was isolated by the appropriate work-up. Examples:

Compound III.1: The reaction mixture was poured into 1 l of a 1%-solution of acetic acid. The product precipitated from the medium. After filtration, the product was treated with refluxing methanol, isolated by filtration, washed with methanol, and dried under reduced pressure.

Compound III.2: The reaction mixture was poured into 200 ml of water. The crude product was isolated by filtration and recrystallized from ethanol.

Preparation Procedure E'

Compound III.8: 9.45 g (0.05 mol) of compound II.1 was suspended in 50 ml of acetonitrile. 11.04 g (0.06 mol) of 2-sulphobenzoic anhydride was added. 5.06 (0.0625 mol) of pyridine was added dropwise while the temperature was kept below 25° C. The product was precipitated with 150 ml of ethyl acetate. The oily residue was redissoved in methanol and treated with 9 ml of a 30%-solution of sodium methanolate in methanol. The sodium salt precipitated from the medium, was isolated by filtration, washed with methanol, and dried under reduced pressure.

Scheme I

I.1

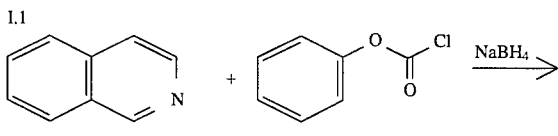

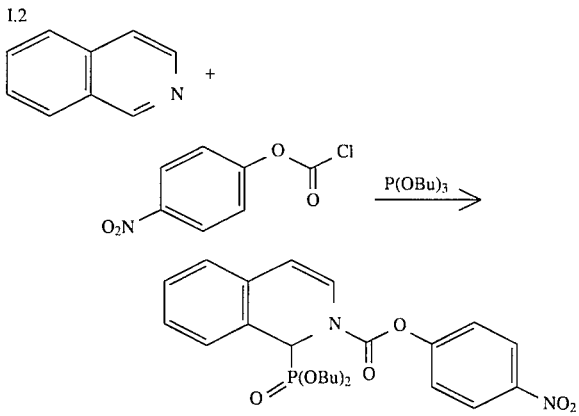

yield: 45%, m.p.: 98° C.
preparation method A

I.2

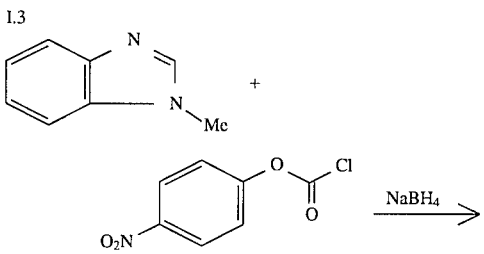

yield: 97%; oil
preparation method B

I.3

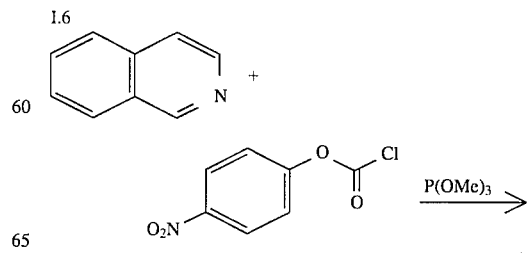

-continued
Scheme I

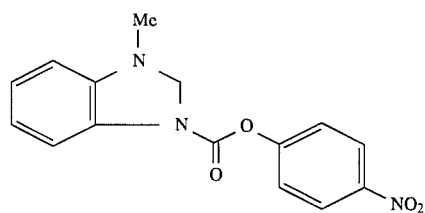

yield: 40%; m.p.: 124° C.
preparation method A

I.4

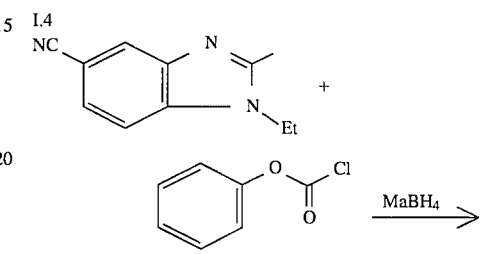

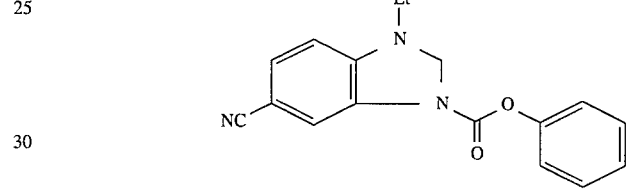

yield 50%; m.p.: 122° C.
preparation method A

I.5

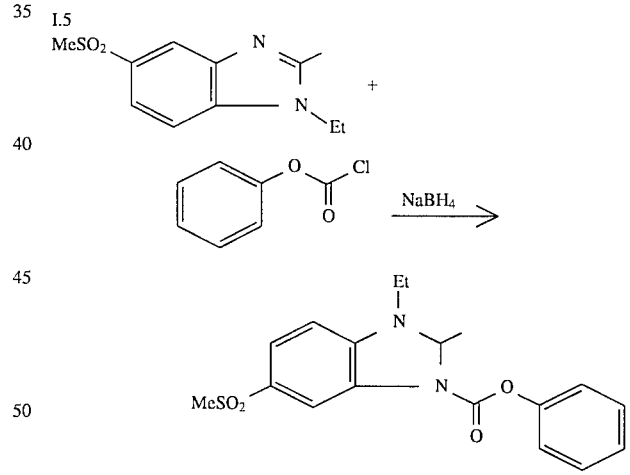

yield: 71%; further used as
crude product
preparation method A

I.6

Scheme I -continued
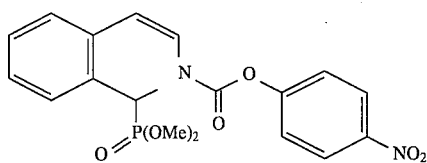
yield: 44%
preparation method B
I.7
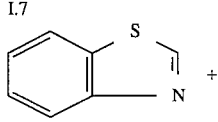
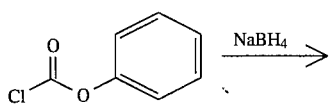
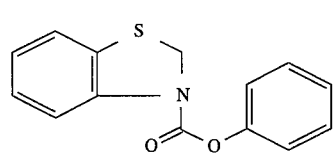
yield: 60%; m.p.: 66° C.
preparation method A
I.8/I.9
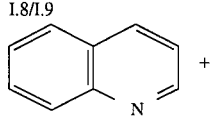
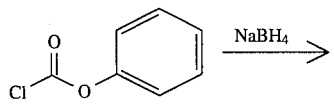
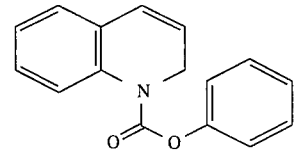 (I-8)
+
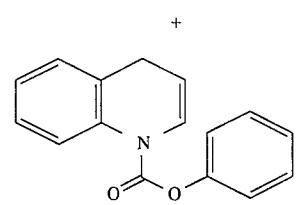 (I-9)
yield: 96%; I.8/I.9 = 5/1
preparation method A
I.10/I.11
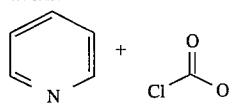 + 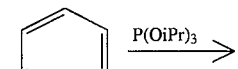 $\xrightarrow{P(OiPr)_3}$
Scheme I -continued
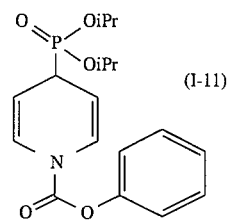 (I-11) I-10
y: 29%
+
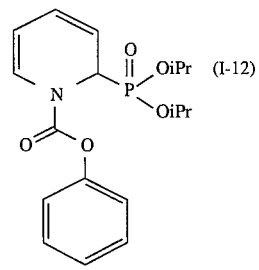 (I-12) I-11
y: 50% oil
preparation method B
Scheme II
II.1
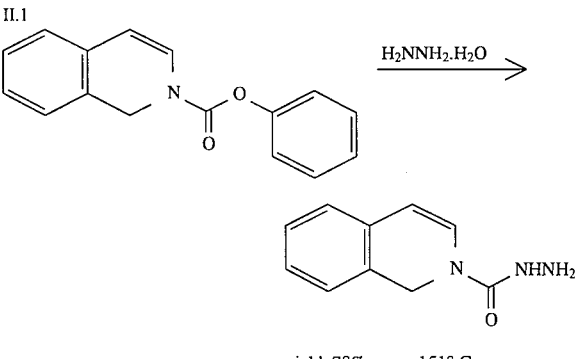
yield: 78%, m.p.: 151° C.
II.2
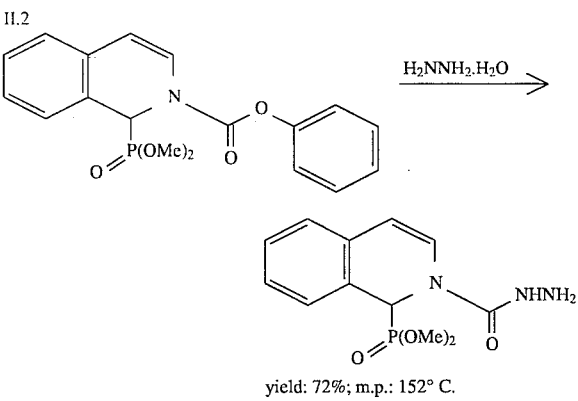
yield: 72%; m.p.: 152° C.
II.3

19
-continued
Scheme II
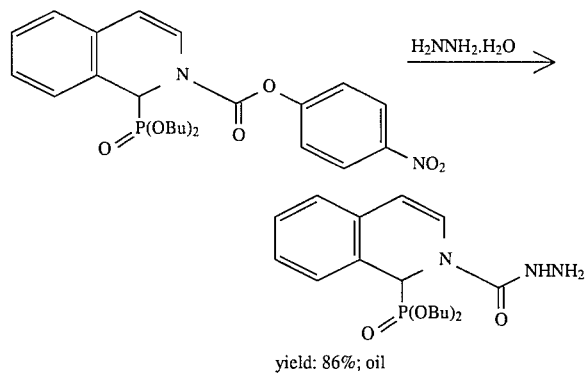
II.4
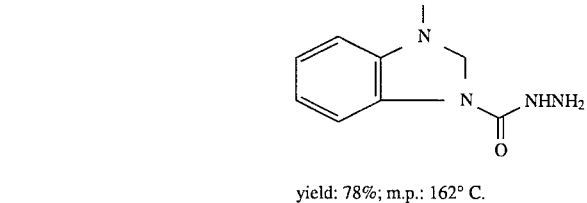
II.5
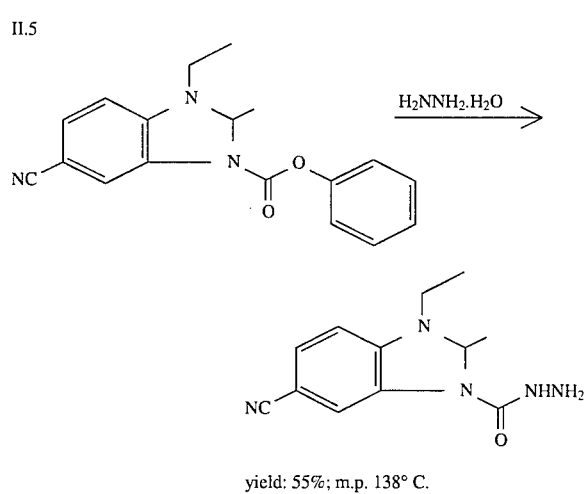
II.6
20
-continued
Scheme II
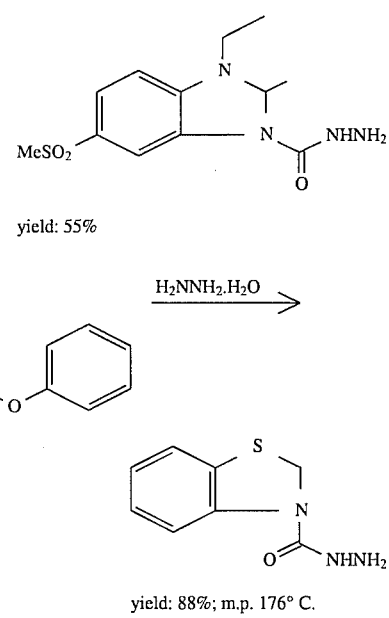
II.7
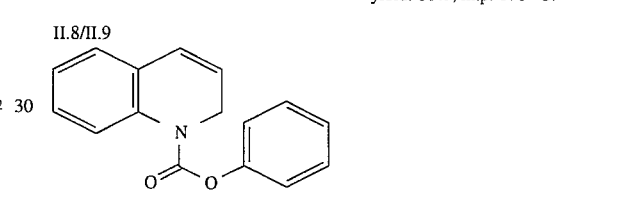
II.8/II.9
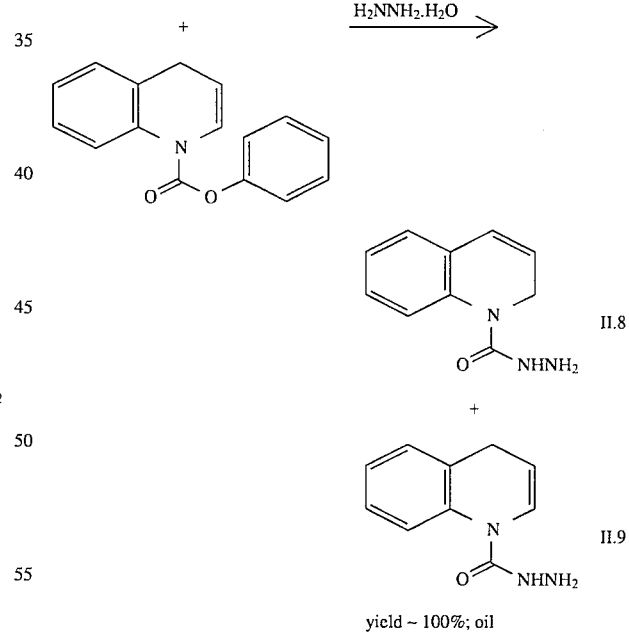
II.10

-continued
Scheme II
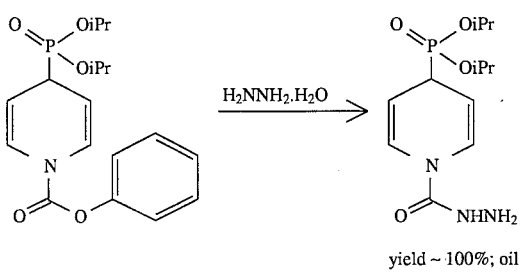
yield ~ 100%; oil
II.11
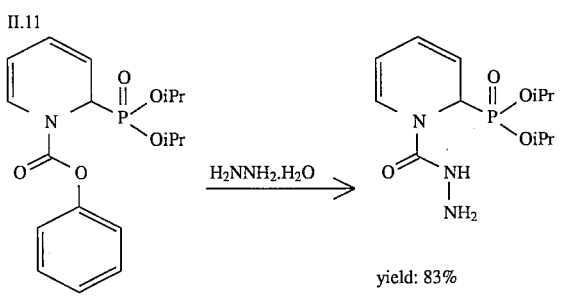
yield: 83%
Scheme III
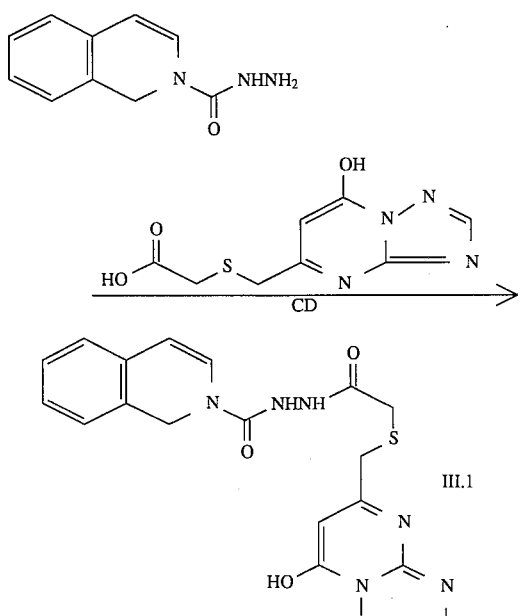
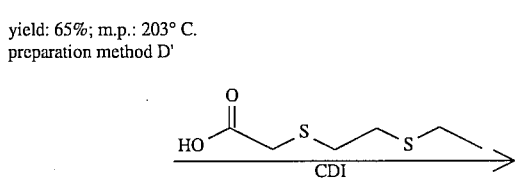
yield: 65%; m.p.: 203° C.
preparation method D'
-continued
Scheme III
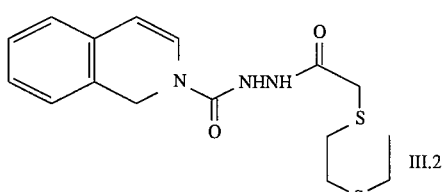
III.2
yield: 60%; m.p. 106° C.
preparation method D'
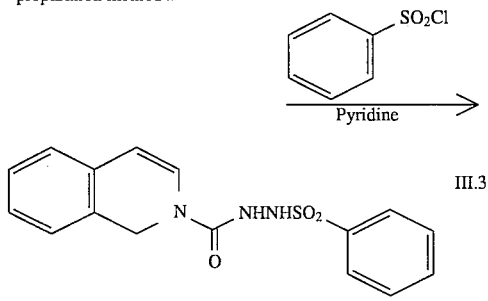
III.3
yield: 96%; m.p. 182° C.
preparation method A'
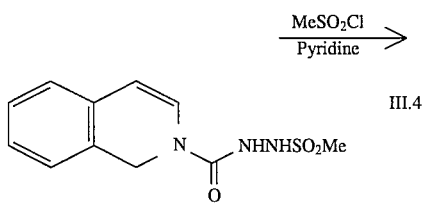
III.4
52%; m.p. 210–212° C.(dec.)
preparation method A'
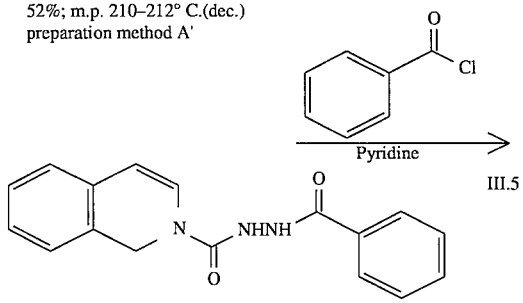
III.5
yield: 90%; m.p. 170° C.
preparation method A'
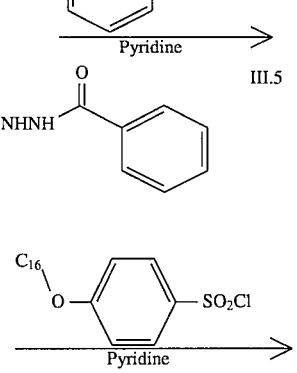
III.6
yield: 82%; m.p.: 132° C.
preparation method B'

-continued
Scheme III
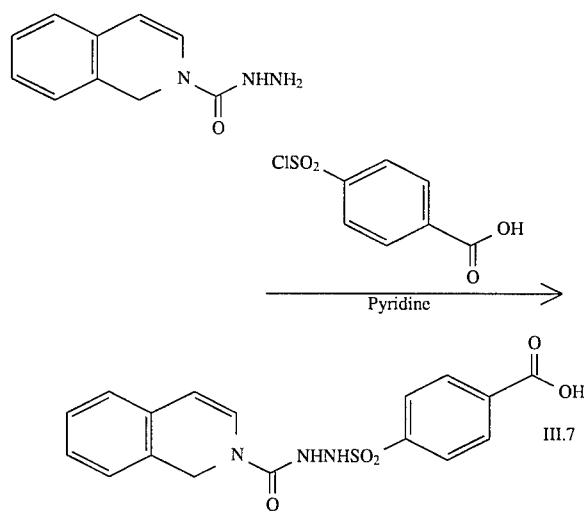
yield: 40%; m.p.: 220° C. (dec.)
preparation method C'
yield: 61%;
m.p.: >260° C.
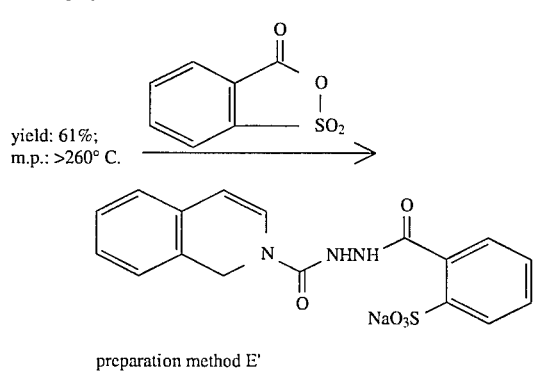
preparation method E'
III.15
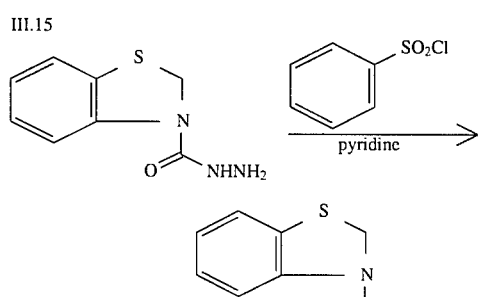
yield: 37%; m.p. 205° C.
preparation procedure A'
III.16/III.17
preparation procedure A'
-continued
Scheme III
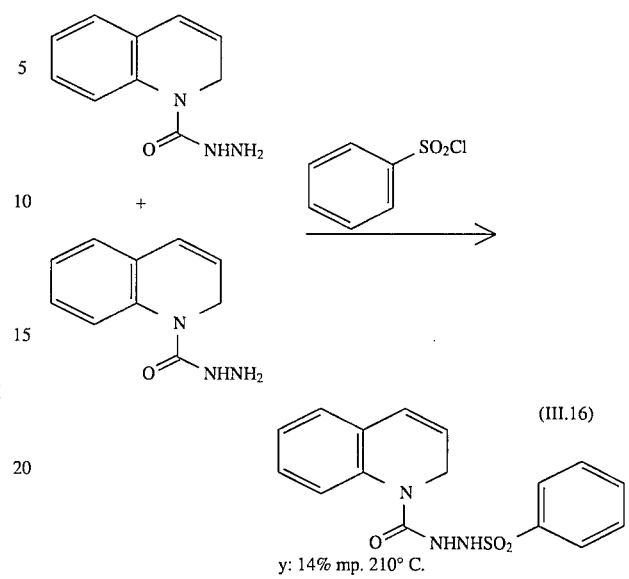
(III.16)
y: 14% mp. 210° C.
(III.17)
y: 2% mp. 165° C.
III.18
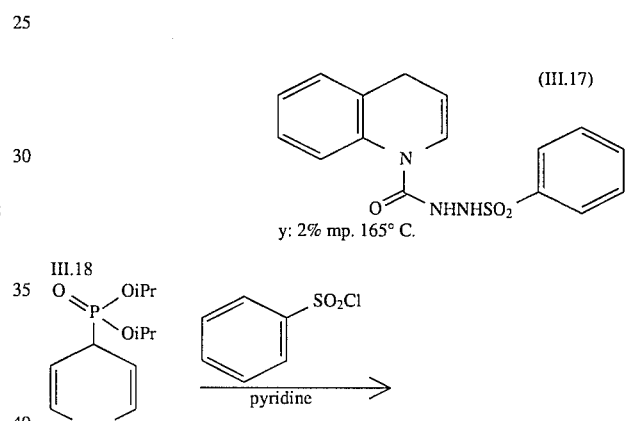
yield: 54%; m.p. 180° C.
preparation procedure A'
III.19
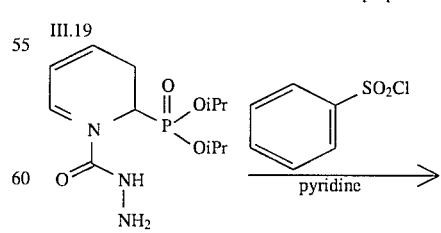

-continued
Scheme III
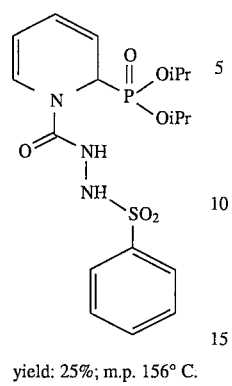
yield: 25%; m.p. 156° C.
preparation procedure A'
Scheme IV
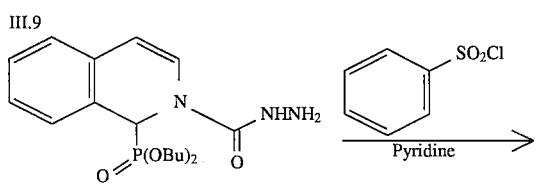
yield: 68%; m.p. 130° C.
preparation procedure A'
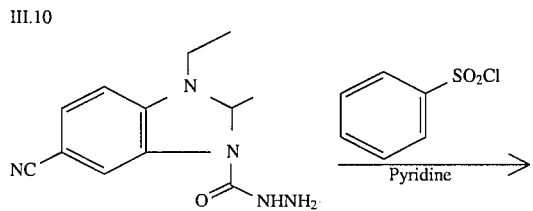
yield: 94%; m.p. 200° C.
preparation procedure A'
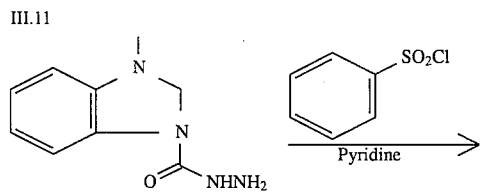
-continued
Scheme IV
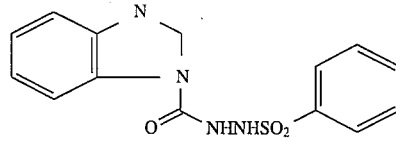
yield: 40%; m.p.: 214° C.(dec.)
preparation procedure A'
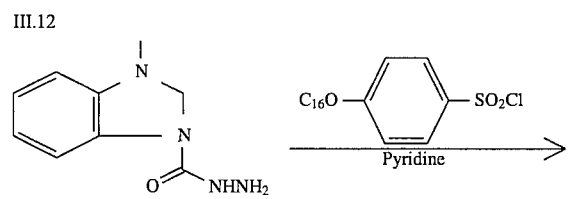
yield: 29%; m.p. 110° C.
preparation procedure B'
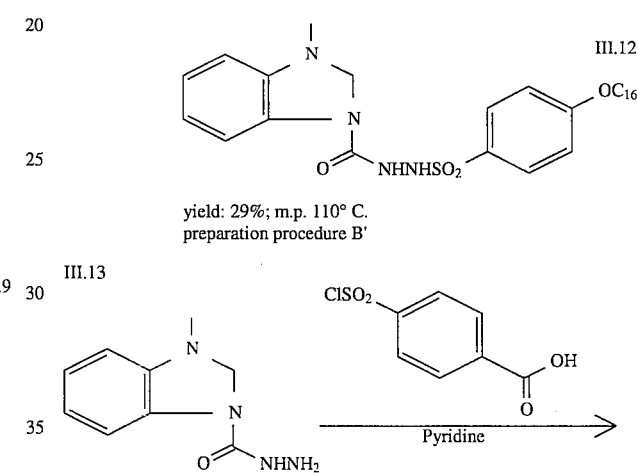
yield: 53%; m.p. > 260° C.
preparation procedure C'
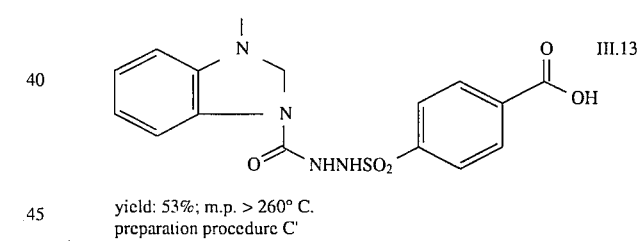
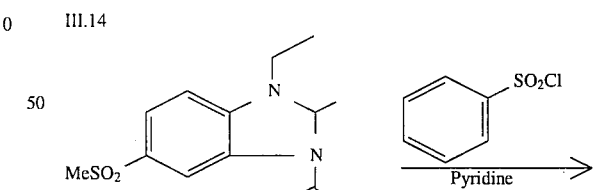
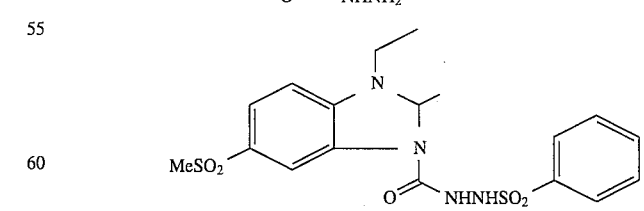
yield: 90%; m.p. 190° C.
preparation procedure A'

B. Examples of Photographic Evaluation

EXAMPLE B.1

A silver chlorobromoiodide emulsion composed of 98% chloride, 1.8% bromide and 0.2% iodide was prepared by the double-jet precipitation method. The average silver halide grain size was 0.3 μm (diameter of a sphere with equivalent volume) and contained rhodium as internal dopant. The emulsion was chemically ripened by adding $1.456 \times 10^{-5}$ mol of $HAuCl_4$, $6 \times 10^{-5}$ mol of $Na_2S_2O_3$ and $10^{-2}$ mol of p-toluenesulphinic acid and by stirring it for 15 min at 60° C. The resulting emulsion was precipitated by adding polystyrenesulphonic acid. The precipitate was rinsed several times and redispersed by adding 150 g of gelatin to obtain a final content of 200 g of $AgNO_3$ per kg of emulsion. The resulting emulsion was stabilized by 5-methyl-1,2,4-triazolo[1,5-a]pyrimidine-7-ol.

The emulsion was coated onto a polyethylene terephthalate support provided with a subbing layer. The emulsion was coated at a silver halide coverage of 2 g $Ag/m^2$, expressed as $AgNO_3$, and the gelatine at a coverage of 3.6 $g/m^2$. The coated layer further contained per $m^2$:
1 mg of 1-phenyl-5-mercaptotetrazole
22 mg of 2-mercapto-7-sulphonato-naphth(2,3-D)oxazole sodium salt
0.5 ml of 4% formaldehyde solution
12.5 ml of commercial wetting agent TERGITOL 4
22.5 ml of commercial wetting agent AKYPO OP80
2.5 mg of perfluorocaprilic acid ammonium salt
a compound specified in Table I (added as a 5%-dispersion (w/w) in gelatine):
The coating solution was adjusted to pH 4.0.

TABLE 1

| photographic element | compound | g/m² |
| --- | --- | --- |
| A(reference) | — | — |
| B | III.3 | 0.775 |
| C | III.7 | 0.878 |
| D | III.6 | 1.34 |
| E | III.5 | 0.688 |
| F | III.14 | 0.905 |
| G | III.9 | 1.03 |

All coated photographic samples were exposed on a sensitometer equipped with a tungsten light source through a step wedge having a wedge constant of 0.15 and processed in a developer having the following composition:
20 g/l of $K_2CO_3$
2 g/l of NaOH
1 g/l of $Na_2SO_3$
0.325 g/l of N,N-diethyl-N',N'-di(2-hydroxyethyl)-p.-phenylene diamine dichlorohydrate
5.5 g/l of hydroquinone
processing time: 60 s; processing temperature: 25° C.

The samples were fixed in a conventional fixer containing ammonium thiosulphate, washed and dried. The sensitivity results (expressed as relative log H, lower figure meaning higher sensitivity) are summarized in table 2:

TABLE 2

| photographic element | sensitivity log H |
| --- | --- |
| A | 1.60 |
| B | 1.125 |
| C | 0.99 |

TABLE 2-continued

| photographic element | sensitivity log H |
| --- | --- |
| D | 1.08 |
| E | 1.08 |
| F | 1.18 |
| G | 1.11 |

As table 2 shows the introduction of the claimed compounds resulted in a significant increase in sensitivity.

EXAMPLE B.2

The same coating solution as described in example B.1 was used for the preparation of the following photographic elements, containing a compound as specified in table 3, added as a 5%-dispersion (w/w) in gelatine:

TABLE 3

| photographic element | compound | g/m² |
| --- | --- | --- |
| A (reference 1) | — | — |
| E | III.5 | 0.688 |
| H (reference 2) | I.1 | 0.59 |
| I (reference 3) | see below | 0.59 |

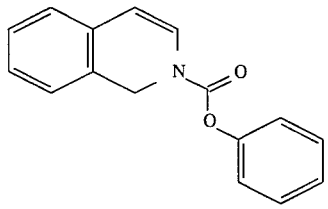

compound I.1

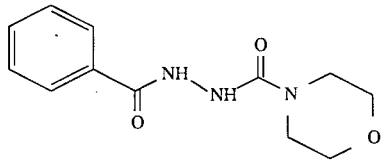

compound ref. 3

The photographic elements were exposed and processed under the same conditions as in example B.1. The sensitivity of the photographic elements is given in table 4.

TABLE 4

| photographic element | sensitivity log (It) |
| --- | --- |
| A | 1.60 |
| E | 1.08 |
| H | 1.53 |
| I | 1.57 |

As illustrated in table 4, only the combination of a hydrazide moiety with an N-acyl-dihydro-heterocycle gives a significant increase in sensitivity.

EXAMPLE B.3

The same emulsion as in the preceding examples was used. The photographic samples were prepared as follows. Onto a polyethylene terephthalate film support coated with a subbing layer was coated a layer with the above described emulsion at a coverage of 2 g of $AgNO_3$ per $m^2$.

Four samples were prepared:
(J) a reference sample:
(K) a sample with $10^{-3}$ mol of compound III.1 per mol of $AgNO_3$;
(L) a reference sample with $2\times10^{-4}$ mol per mol of $AgNO_3$ of the green spectral sensitizer SS-1 (see formula below):
(M) a sample with $2\times10^{-4}$ mol of the spectral sensitizer SS-1 per mol $AgNO_3$ and $10^{-4}$ mol of compound III.1 per mol $AgNO_3$.

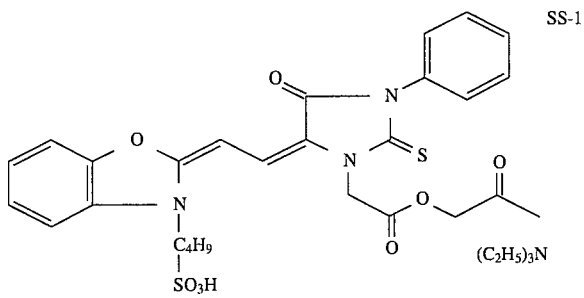

The samples were exposed by means of a sensitometer equipped with a tungsten light source, developed in a conventional rapid access Phenidone-hydroquinone developer for 30 s at room temperature, fixed, rinsed and dried. The sensitivities, measured at 0.7 density+$D_{min}$, are shown in table 5. The values for the gradation between densities 0.2+$D_{min}$ and 1.0+$D_{min}$ were the same within ±7% for the four samples.

TABLE 5

| sample | sensitivity |
|---|---|
| J | 194 |
| K | 160 |
| L | 99 |
| M | 85 |

Table 5 again illustrates the sensitivity gain obtained with the invention compound with and without spectral sensitization.

We claim:

1. Photographic material comprising a support and at least one silver halide emulsion layer, characterized in that said at least one emulsion layer contains a compound according to general formula (A):

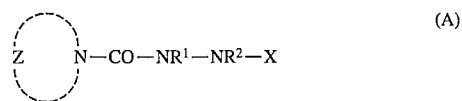

wherein

Z represents the necessary atoms to close a heterocyclic ring which is either a five-membered ring containing at least two heteroatoms or a six-membered ring, which ring may carry one or more fused-on rings, and which ring must contain a C—H bond permitting oxidative aromatisation to an acyl-onium group by means of a hydride shift or a consecutive 2-electron-proton transfer; each of $R^1$ and $R^2$ independently represents a hydrogen atom or an alkali-labile group giving rise to a hydrogen atom on hydrolysis;

X is an acyl group selected from the group consisting of CO—$R^3$, CS—$R^4$, $SO_2$—$R^5$, PO—$R^6R^7$ and (CN—$R^8$)—$R^9$, wherein each of $R^3$ to $R^9$ independently represents alkyl, aryl, cycloalkyl, heterocycloalkyl, heteroaryl, O-alkyl, O-aryl, O-heteroaryl, O-heterocycloalkyl, S-alkyl, S-aryl, S-heterocycloalkyl, S-heteroaryl or N—$R^{10}R^{11}$, wherein each of $R^{10}$ and $R^{11}$ independently represents hydrogen, aryl, alkyl, heteroaryl, heterocycloalkyl or acyl as defined for X, and wherein $R^6$ together with $R^7$, and $R^{10}$ together with $R^{11}$ may represent the necessary atoms to close a ring.

2. Photographic material according to claim 1, wherein said heterocyclic ring is chosen from the group consisting of pyridine, imidazole, thiazole, pyrazine, N-alkylpyrrole, oxazole, pyrimidine, N-alkyltriazole, oxadiazole, thiadiazole, pyridiazines, isoxazoles, isothiazoles and selenazoles, wherein these heterocyclic rings may carry fused-on rings.

3. Photographic material according to claim 2, wherein said heterocyclic ring is selected from the group consisting of isochinoline, and benzimidazole.

4. Photographic material according to claim 1, wherein said compound according to general formula (A) is incorporated in said at least one emulsion layer in a concentration between $10^{-6}$ mol and $2\times10^{-1}$ mol per mol of silver halide.

5. Photographic material according to claim 1, wherein one of $R^3$ to $R^{11}$ is a moiety capable of forming a low-soluble salt or a complex with silver ions.

6. Photographic material according to claim 5, wherein said moiety is a tetraazaindene moiety.

* * * * *